United States Patent [19]
Kinoshita et al.

[11] Patent Number: 5,922,284
[45] Date of Patent: Jul. 13, 1999

[54] METHOD AND APPARATUS FOR AGGLUTINATION IMMUNOASSAY

[75] Inventors: Yoshihiro Kinoshita, Ome; Kazunori Soma, Tokorozawa; Tomoo Saito, Kawasaki, all of Japan

[73] Assignee: Fujirebio Inc., Tokyo, Japan

[21] Appl. No.: 09/081,017

[22] Filed: May 19, 1998

Related U.S. Application Data

[62] Division of application No. 08/643,457, May 8, 1996, Pat. No. 5,817,526.

[30] Foreign Application Priority Data

May 9, 1995 [JP] Japan ................................. 7-110960
May 9, 1995 [JP] Japan ................................. 7-110962

[51] Int. Cl.⁶ .......................................... G01N 33/553
[52] U.S. Cl. .................... 422/68.1; 422/73; 422/82.01; 422/82.08; 435/287.1; 435/287.2; 435/288.7; 435/808; 436/164; 436/514; 436/523; 436/524; 436/525; 436/526; 436/536; 436/805; 210/222; 210/223
[58] Field of Search ...................... 422/68.1, 73, 82.01, 422/82.08; 435/287.1, 287.2, 288.7, 808; 436/514, 524, 525, 526, 536, 523, 164, 805; 210/222, 223

[56] References Cited

U.S. PATENT DOCUMENTS

| | | | |
|---|---|---|---|
| 4,992,377 | 2/1991 | Saxholm | 436/808 |
| 5,158,871 | 10/1992 | Rossomando et al. | 435/7.32 |
| 5,202,269 | 4/1993 | Ito et al. | 436/526 |
| 5,476,796 | 12/1995 | Takahashi et al. | 436/526 |
| 5,536,475 | 7/1996 | Moubayed et al. | 422/101 |
| 5,602,042 | 2/1997 | Farber | 436/526 |

FOREIGN PATENT DOCUMENTS

| | | | |
|---|---|---|---|
| 0522322 | 1/1993 | European Pat. Off. | 436/526 |
| 4369477 | 12/1992 | Japan | 436/526 |

*Primary Examiner*—Christopher L. Chin
*Attorney, Agent, or Firm*—Oblon, Spivak, McClelland, Maier & Neustadt, P.C.

[57] ABSTRACT

An agglutination immunoassay method and apparatus therefor in which there are conducted the steps of contacting, in a container, a test sample suspected of containing a desired analyte and a reagent comprising sensitized magnetic-material containing particles capable of reacting with and binding to a desired analyte; precipitating the particles on the bottom of the container by the application of magnetic force; allowing the container to stand at an inclination so as to cause the particles to flow along the bottom of the container to form a developed pattern of the particles; obtaining a representative length of the developed pattern of the particles by an imaging device; and detecting the presence or absence of an immune reaction from the representative length of the pattern of the particles which has flowed from the bottom of the container, thereby detecting the presence or absence of the desired analyte in the test sample.

2 Claims, 10 Drawing Sheets

AXIS OF DEVELOPED PATTERN

FIG. 7(B)

AXIS OF DEVELOPED PATTERN

FIG. 8

| 157 | 168 | 179 | 191 | 208 | 222 | 241 | 255 | 255 |
|---|---|---|---|---|---|---|---|---|
| 112 | 127 | 142 | 159 | 172 | 180 | 193 | 210 | 230 |
| 87 | 92 | 110 | 127 | 136 | 139 | 156 | 170 | 201 |
| 109 | 119 | 131 | 147 | 161 | 182 | 203 | 217 | 239 |
| 156 | 162 | 173 | 191 | 199 | 211 | 232 | 243 | 249 |

FIG. 9

| 1 | 1 | 1 | 1 | 1 | 1 | 1 | 1 | 1 |
|---|---|---|---|---|---|---|---|---|
| 0 | 0 | 0 | 1 | 1 | 1 | 1 | 1 | 1 |
| 0 | 0 | 0 | 0 | 0 | 0 | 1 | 1 | 1 |
| 0 | 0 | 0 | 0 | 1 | 1 | 1 | 1 | 1 |
| 1 | 1 | 1 | 1 | 1 | 1 | 1 | 1 | 1 |

FIG. 10

METHOD AND APPARATUS FOR AGGLUTINATION IMMUNOASSAY

This application is a Division of application Ser. No. 08/643,457, filed on May 8, 1996, now U.S. Pat. No. 5/817,526.

BACKGROUND OF THE INVENTION

1. Field of the Invention

The present invention relates to a method and apparatus for conducting agglutination immunoassay by containing, in a container, a test sample suspected of containing a desired analyte and a reagent which comprises magnetic-material containing particles, which have been sensitized to permit specific binding to the desired analyte.

2. Discussion of Background

Conventionally, agglutination immunoassay has been conducted by utilizing agglutination reaction which is caused to occur by antigen-antibody reaction to detect the presence or absence of the desired analyte such as an antibody or antigen in the test sample.

It is possible to detect whether or not such an agglutination reaction occurs by allowing the mixture of the test sample and the reagent to stand stationarily for a while and to then inspect the state or shape of an agglutination pattern composed of the sensitized particles on which the antigen or antibody is bound or immobilized, or the state or shape of unbound reagent.

Such conventional immunoassay, however, is not quick and the mixture of the test sample and the reagent must be maintained for some time under conditions completely free from vibrations.

Under such circumstances, the Applicants of the present invention have proposed an agglutination immunoassay in European Patent 426170. In the agglutination immunoassay, the test sample suspected of containing the desired analyte is contacted with a reagent comprising magnetic-material containing particles, which have been sensitized to permit specific binding to the desired analyte, in a container such as wells of microtiter plate.

In the agglutination immunoassay, the analyte is bound or immobilized on the sensitized particle. The magnetic-material containing particles, which have bound to the desired analyte, are magnetically precipitated to the bottom of the container by application of magnetic force.

After precipitation, the container in which the contact occurs is allowed to stand at an inclination.

On inclination, the precipitated particles will flow under the effect of gravity if no immune binding reaction has occurred. The absence of flow indicates that the desired analyte is present and bound to the sensitized particles. Thus, by the presence or absence of such a flowed developed pattern (hereinafter referred to as a developed pattern), the presence or absence of the agglutination reaction, and accordingly the presence or absence of the desired analyte is judged. This assay is quick and reliable for a large number of test samples.

In order to further speed up this assay, and also to make this assay more reliable without depending upon operators' individual skill, the Applicants of the present invention have further proposed in European Application 625708A a high speed automated apparatus for the assay by use of an optical sensor which is capable of detecting the shape of the developed pattern of the precipitated particles at the bottom of each well of microtiter plate.

More specifically, in the apparatus, there is provided a line optical sensor comprising micro optical sensors which are arranged side by side in the extending direction of the line optical sensor, in the same number as that of the wells in each column of the microtiter plate, in such a manner that each micro optical sensor can measure the length of a crossing portion of a line that crosses the developed pattern in a predetermined direction in the corresponding well.

In order to detect the shape of the developed pattern accurately, the line optical sensor is moved to the right and left for the sample in each well so that the measurement of the length of the crossing portion of the line is carried out at three representative points in total.

In this method, the above-mentioned measurement is carried out for each developed pattern. However, unless the positioning of the measurement for the three lines is carried out appropriately and accurately for each developed pattern, the shape of the developed pattern cannot be detected accurately. Therefore, it is required that the positioning of the measurement for the three lines be made appropriately and accurately. Furthermore, it is required that the number of the lines to be measured be maximized.

However, the greater the number of the lines for the measurement of the length, the longer the time required for the assay; and more accurate operating means is required for handling the microtiter plates and the optical sensor in order to perform accurate and appropriate positioning of the measurement of the length of the three lines.

The Applicants of the present invention have further proposed in Japanese Laid-Open Patent Application 5-297001 an apparatus for the above-mentioned immunoassay, which utilizes a CCD camera for detecting the shape of the previously mentioned developed pattern in agglutination immunoassay.

More specifically, in the above apparatus, image signals are obtained by the CCD camera from the microtiter in its entirety and processed so as to calculate the length of each developed pattern from the changes in luminance detected from the obtained image signals.

The values obtained by this apparatus, however, so scatter that reliable detection data cannot always be provided with respect to the shape of the developed pattern.

SUMMARY OF THE INVENTION

It is therefore a first object of the present invention to provide a method of conducting agglutination immunoassay, which is quick, reliable, easily inspected and automated, and useful in a wide variety of assays, from which the above-mentioned shortcomings of the conventional methods have been eliminated.

A second object of the present invention is to provide an apparatus for conducting the above-mentioned agglutination immunoassay.

The first object of the present invention is achieved by an agglutination immunoassay comprising the steps of:

contacting, in a container, a test sample suspected of containing a desired analyte and a reagent comprising sensitized magnetic-material containing particles capable of reacting with and binding to the desired analyte;

precipitating the sensitized magnetic-material containing particles on the bottom of the container by the application of magnetic force;

allowing the container to stand at an inclination so as to cause the precipitated sensitized magnetic-material containing particles to flow along the bottom of the container to form a developed pattern of the precipitated sensitized magnetic-material containing particles;

obtaining a representative length of the developed pattern of the precipitated sensitized magnetic-material containing particles in the flowing direction thereof, from image data of the developed pattern obtained by imaging means; and detecting the presence or absence of an immune reaction from the representative length of the developed pattern, thereby detecting the presence or absence of the desired analyte in the test sample.

In the above agglutination immunoassay, the magnetic-material containing particles may have immobilized thereon an antigen or antibody which specifically binds to the desired analyte.

Furthermore, in the agglutination immunoassay, the imaging means may comprise a CCD camera.

In the above agglutination immunoassay, the image data of the developed pattern obtained by the imaging means may comprise image pixel data in the flowing direction of the developed pattern, which is referred to as direction Y, and image pixel data in the direction normal to the direction Y, which is referred to as direction X.

Furthermore, in the above agglutination immunoassay, the image pixel data in both the direction X and direction Y may be converted into digital image signal data, and the representative length of the developed pattern may be represented by digital image signal data in the direction Y.

Further, the representative length of the developed pattern may be obtained by a logical sum of a plurality of digital signal data selected from the digital signal data in the direction Y.

The second object of the present invention is achieved by an apparatus for agglutination immunoassay which comprises:

pipetting means for contacting, in a container, a test sample suspected of containing a desired analyte and a reagent comprising sensitized magnetic-material containing particles capable of reacting with and binding to the desired analyte;

magnetic precipitation means for precipitating the sensitized magnetic-material containing particles on the bottom of the container by the application of magnetic force;

inclination means for allowing the container to stand at an inclination so as to cause the precipitated sensitized magnetic-material containing particles to flow along the bottom of the container to form a developed pattern of the precipitated sensitized magnetic-material containing particles;

imaging means for imaging the developed pattern to obtain image data thereof and obtaining from the image data a representative length of the developed pattern of the precipitated sensitized magnetic-material containing particles in the flowing direction thereof; and immune reaction detection means for detecting the presence or absence of an immune reaction from the representative length of the developed pattern, thereby detecting the presence or absence of the desired analyte in the test sample.

In the above apparatus, the imaging means may comprise a CCD camera.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

With reference to the accompanying drawings, the present invention will now be explained in more detail.

Figure 1:
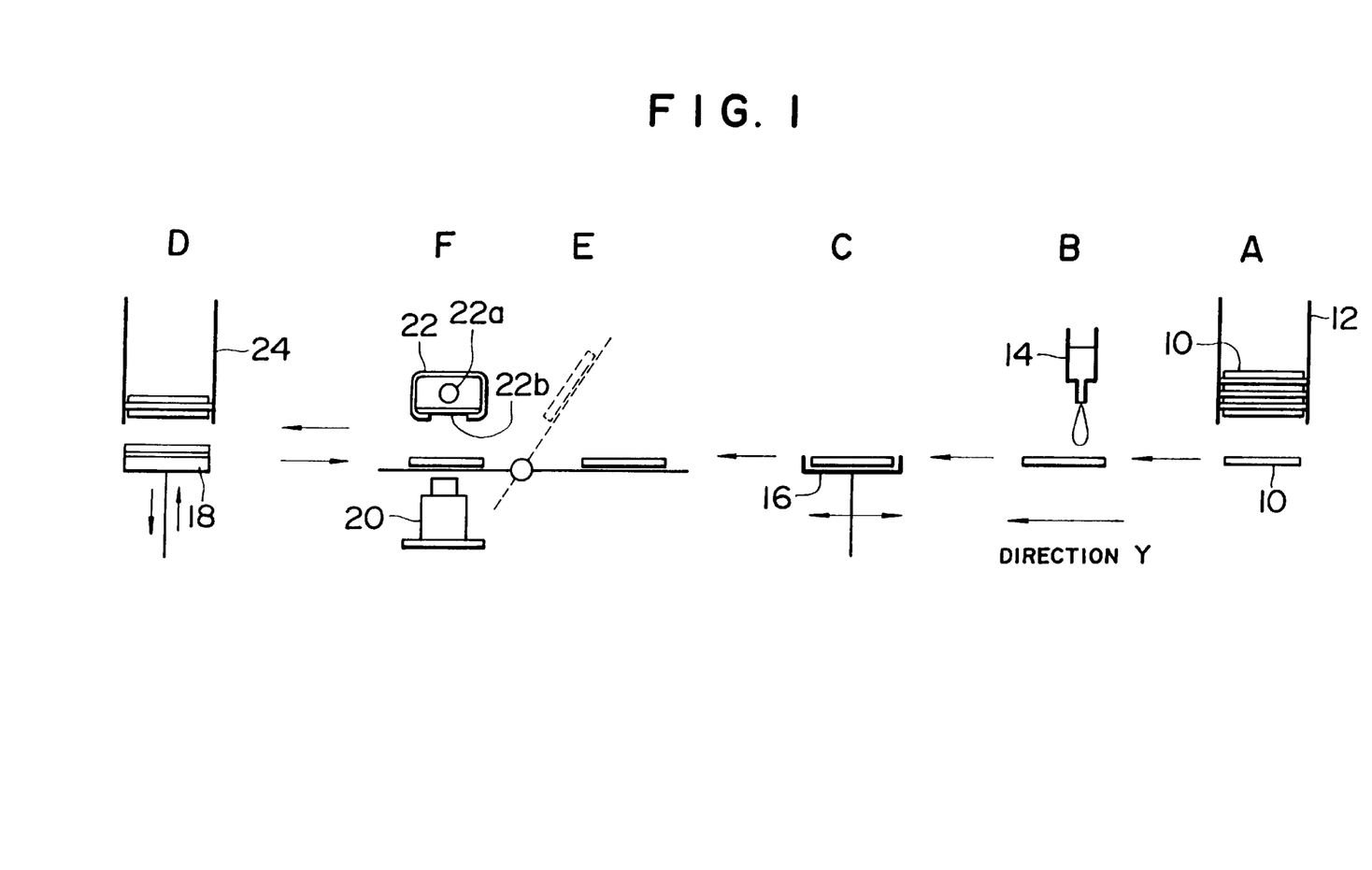
FIG. 1 is a schematic diagram in explanation of the operation of an agglutination immunoassay system of the present invention.

FIG. 1 shows a schematic diagram in explanation of an agglutination immunoassay system of the present invention.

Reference numeral 10 shows a microtiter plate including a number of wells. In the microtiter plate 10, for example, there are provided 96 wells in an 8×12 matrix, that is, 8 wells in the direction Y, and 12 wells in the direction X.

A number of the microtiter plates 10, with a test sample being injected into each well thereof, are held in a supply stack 12 in a supply station A.

The microtiter plates 10 are successively transported one by one to a pipetting station B where an agglutination reagent is pipetted into each well of the microtiter plate 10.

More specifically, a pipetting unit 14 is moved onto each well of the microtiter plate 10 by driving means (not shown), and a predetermined amount of the reagent is successively added to each of the wells of the microtiter plate 10.

When it is supposed that the direction vertical or normal to the plane of this figure is X (not shown), and the direction normal to the direction X is Y, a first well in the first column of the microtiter plate 10 is positioned right under the pipetting unit 14, and the reagent is pipetted into the first well. The pipetting unit 14 is then successively moved in the direction X and the reagent is successively pipetted into the wells in the first column of the microtiter plate 10.

The microtiter plate 10 is then moved in the direction Y in such a manner that the second column in the microtiter plate 10 comes right under the pipetting unit 14. The reagent is successively pipetted into the wells in the second column of the microtiter plate 10 by the pipetting unit 14 in the same manner as mentioned above.

The same operation is repeated so that the reagent is pipetted into all of the wells of the microtiter plate 10.

This reagent comprises magnetic-material containing particles having immobilized thereon an antigen or antibody which specifically binds to the desired analyte.

Therefore, by detecting the presence or absence of an immune reaction when this reagent is mixed with a test sample, the presence or absence of an antibody or antigen in the test sample is detected.

Furthermore, since the particles in this reagent contains a magnetic material such as ferrite, magnetic force has an effect on the particles.

An example of a test sample that can be employed in the present invention is a diluted blood serum to check whether or not a specific antibody is present therein.

The amount of such a test sample is, for example, about 25 µl, and the amount of the reagent is also about 25 µl.

When the addition of the reagent to all the wells of the microtiter plate 10 has been finished, the microtiter plate 10 is then transported to an agitation station C, which comprises vibration means 16. The microtiter plate 10 is vibrated by the vibration means 16, so that the mixing of the reagent pipetted in the pipetting station B and the test sample is promoted.

In an example of the present invention, the agitation is performed for about 5 minutes to secure the occurrence of an immune reaction.

The microtiter plate 10 is transported to the agitation station C from the supply station A, for instance, by a transport belt (not shown) to which the microtiter plate 10 is attached thereto through a holder (not shown).

When the agitation of the reagent and the test sample is finished in the agitation station C, the microtiter plate 10 is then transported to a magnetic precipitation and microtiter plate recovery station D, passing over an inclination station E and an imaging station F. In the magnetic precipitation and microtiter plate recovery station D, there is provided a vertically movable magnetic plate 18 including magnets, which are disposed right under each well of the microtiter plate 10, so that the magnetic-material containing particles in the mixture of the reagent and the test sample are magnetically precipitated to the bottom of each well.

In the microtiter plate 10 for use in the present invention, each well thereof has a circular-cone-shaped or V-shaped bottom (hereinafter referred to as V-shaped bottom), so that the particles are magnetically precipitated on the lowermost portion in the center of the V-shaped bottom of each well.

When such magnetic precipitation occurs, the precipitated particles in each well appear as a black spot when viewed form above or from under the well.

Such magnetic precipitation is carried out by positioning the microtiter plate 10 on the magnetic plate 18 for about 1 minute.

When this magnetic precipitation has been finished, the microtiter plate 10 is then transported back to the inclination station E, which is positioned adjacent to the agitation station C.

In the inclination station E, the microtiter plate 10 is allowed to stand at an inclination, for example, at an inclination of 60°, for about 2 minutes.

The precipitated particles are caused to flow along the bottom of the well under the influence of gravity. However, the degree or state of the flow of the precipitated particles largely depends upon whether or not an immune reaction has occurred.

More specifically, when the desired analyte, that is, an antibody or antigen, is present in the test sample and an immune reaction occurs between the analyte and the sensitized magnetic-material containing particles in the reagent, the analyte and the sensitized magnetic-material containing particles agglutinate together.

The agglutinated particles are precipitated by the application of magnetic force thereto. The thus precipitated particles relatively firmly agglutinate together so that even when the particles are allowed to stand at an inclination, the particles hardly flow along the bottom of the well even under the influence of gravity.

In sharp contrast to this, when no immune reaction occurs, the above-mentioned agglutination reaction does not occur. Therefore the precipitated particles are associated very weakly and loosely so that when the particles are allowed to stand at an inclination, the particles readily flow along the bottom of the well under the influence of gravity.

Therefore, when there occurs no immune reaction, that is, when the desired antibody or antigen is not present in the test sample, the particles form a long and narrow spindle-shaped developed pattern when allowed to stand at an inclination.

In this case, even when the well is inclined, it does not occur that the particles flow out of the well because of the surface tension of the liquid containing the particles therein and also because of the small size of the well.

The thus formed spindle-shaped developed pattern, once formed, is not readily returned to its original shape even when the well is returned to its original horizontal position.

Thus, after the microtiter plate 10 is allowed to stand at an inclination for a predetermined period of time, the microtiter plate 10 is transported to the imaging station F.

In the imaging station F, there are provided a CCD camera 20 serving as an imaging device below the microtiter plate 10, and a lighting device 22 above the microtiter plate 10. The microtiter plate 10 is moved between the CCD camera 20 and the lighting device 22.

In the example shown in FIG. 1, the microtiter plate 10 is intermittently moved by a pitch corresponding to the diameter of the well in the direction Y in the imaging station F, whereby the image of the developed pattern of the precipitated particles is determined in each well of the microtiter plate 10 is taken by the CCD camera and output therefrom as image signals. The thus output image signals corresponding to the image of the developed pattern of the precipitated particles in each well are subjected to data processing by a data processing apparatus (not shown) and analyzed, whereby whether or not the suspected antigen or antibody is present in the test sample in accordance with the developed pattern of the sensitized magnetic-material containing particles.

Normally, the moving pitch of the microtiter plate 10 is the same in the directions of both X and Y.

The lighting device 22 comprises a cold cathode tube 22a and a diffuser plate 22b for achieving uniform lighting free from flickering.

When the imaging operation is thus finished, the microtiter plate 10 is again moved onto the magnetic plate 18 in the magnetic precipitation and microtiter plate recovery station D.

A recovery stack 24 is provided above the magnetic plate 18. The microtiter plate 10 placed on the magnetic plate 18 is recovered and placed into the recovery stack 24 by moving the magnetic plate 10 upward.

Thus, in this example, the magnetic plate 18 is disposed below the recovery stack 24, and the microtiter plate 10 can be recovered into the recovery stack 24 by the magnetic plate 18 as mentioned above. In the magnetic precipitation and microtiter plate recovery station D, both the precipitation of the magnetic-material containing particles by the application of magnetic force and the recovery of the microtiter plate 10 can be performed, thereby minimizing the size and space of the agglutination immunoassay system. Furthermore, in this agglutination immunoassay system, the supply stack 12 and the recovery stack 24 are disposed at the opposite ends of this system, so that the supply and recovery of microtiter plates can be smoothly performed easily and automatically, and the supply stack 12 and the recovery stack 24 can also be easily and automatically exchanged with another supply stack and recovery stack, respectively.

Figure 2:
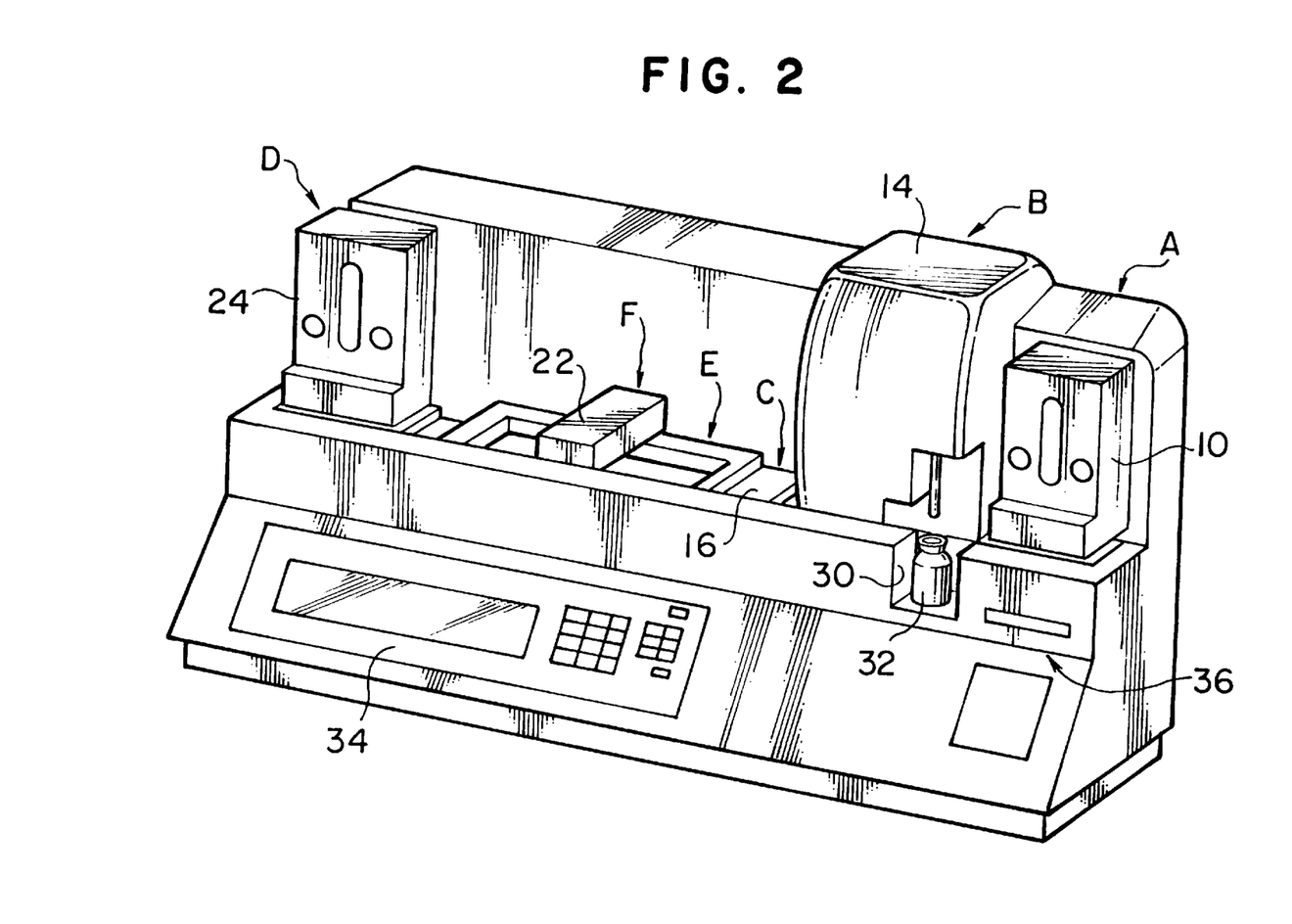
FIG. 2 is a perspective external view of an apparatus incorporating the agglutination immunoassay system of the present invention as shown in FIG. 1.

FIG. 2 is a perspective external view of an apparatus incorporating the above-mentioned agglutination immunoassay system. Reference symbol A indicates the supply station A; reference symbol B, the pipetting station B; reference symbol C, the agitation station C; reference symbol E, the inclination station; reference symbol F, the imaging station; and reference symbol D, the magnetic precipitation and microtiter plate recovery station.

In front of the pipetting station B, there is provided a reagent table 30 on which a reagent bottle 32 is placed.

The pipetting unit 14 sucks a predetermined amount of a reagent from the reagent bottle 32 and insects a predetermined amount of the reagent into each well of the microtiter plate 10.

On the front left side of this apparatus, there is provided an operation panel 34 for various operations, and on the front right side, there is also provided a printer 36 for printing out the results of the assays conducted.

Figure 3:
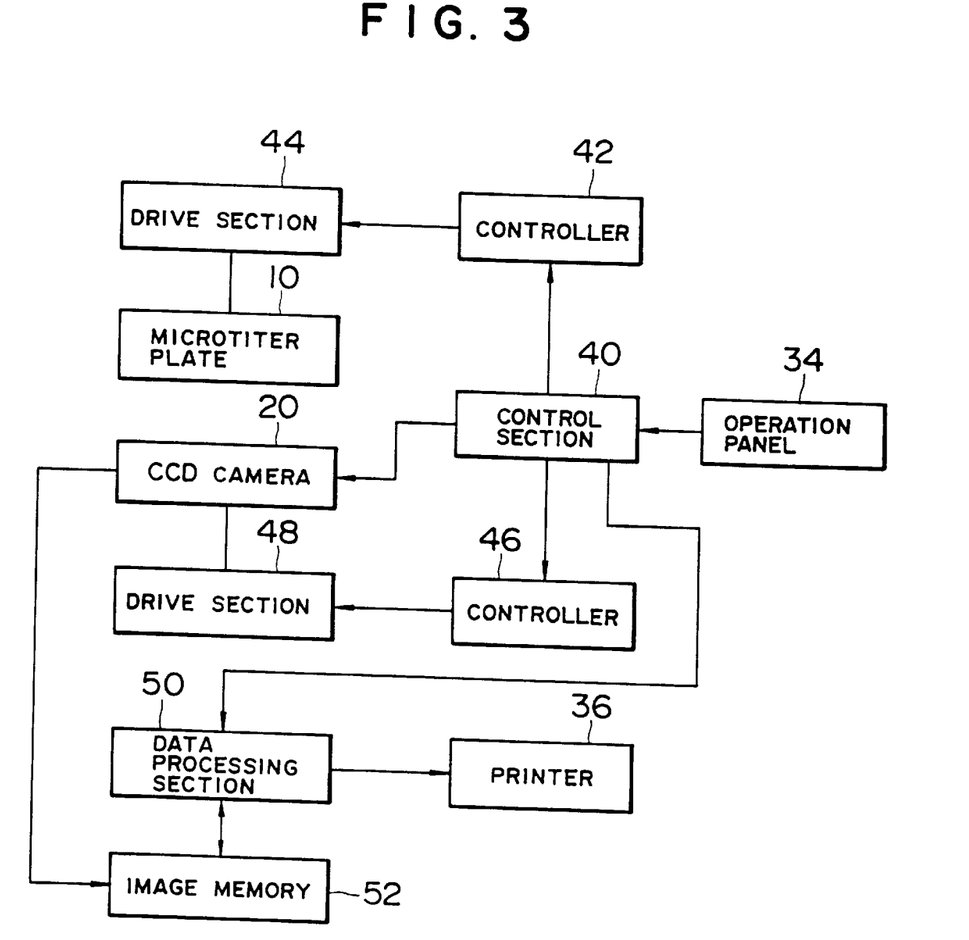
FIG. 3 is a block diagram of the functions of the apparatus shown in FIG. 2.

FIG. 3 is a block diagram of the functions of the apparatus shown in FIG. 2.

A control section 40 is connected to the operation panel 34 and controls various actions of this apparatus. More specifically, a drive section 44 which serves as a microtiter plate driving mechanism is controlled by a controller 42, so that the microtiter plate 10 is transported to a predetermined position.

Furthermore, a drive section 48 which serves as an imaging device moving mechanism is controlled through a controller 46, so that the movement of the CCD camera 20 is controlled.

A control section 40 controls the timing for fetching image data from each well into the CCD camera 20.

An image data memory 52 and a data processing section 50, serving as a shape detection section as well as a judging section, are connected to the CCD camera 20, and process the image data from the CCD camera 20 and judge whether or not an immune reaction has occurred. The results of the judgement are output by the printer 36.

An image memory 52 stores the image data with a capacity of storing image data for at least one well.

Figure 4:
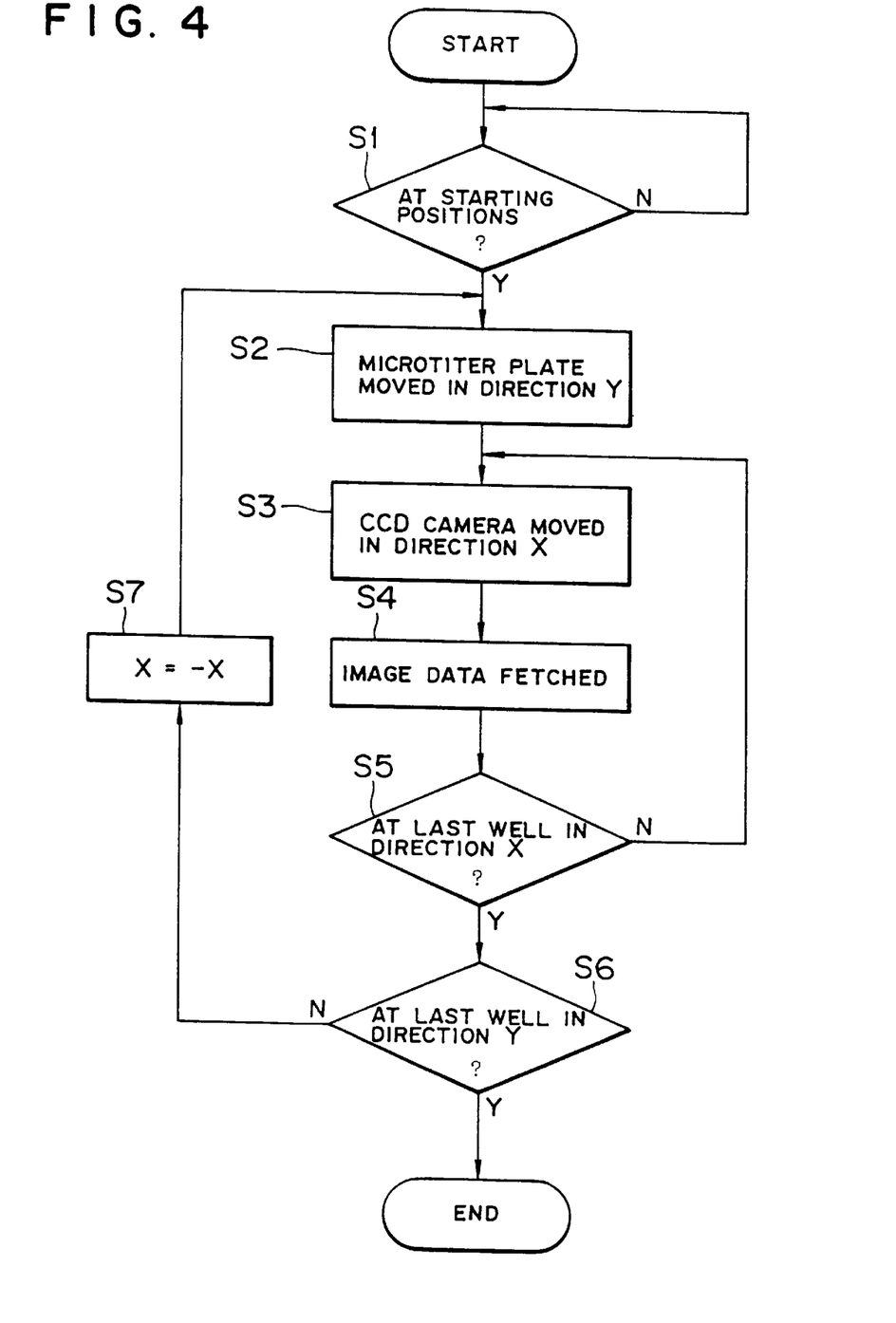
FIG. 4 is a flow chart in explanation of an imaging operation for fetching image data at an imaging station F in the agglutination immunoassay system of the present invention.

With reference to FIG. 4, the imaging operation at the imaging station F will now be explained.

First of all, it is confirmed whether or not the microtiter plate 10 and the CCD camera 20 are positioned at the respective starting positions by step S1.

When it is confirmed that the microtiter plate 10 and the CCD camera 20 are positioned at the respective starting positions, the microtiter plate 10 is moved in the direction Y in such a manner that the wells in the first column in the microtiter plate 10 are positioned right above a predetermined track of the CCD camera 20 by step S2.

The CCD camera 20 is then moved in the direction X in such a manner that the first well comes right above the CCD camera 20 by step S3.

In this state, the image data of the first well is fetched into the data processing section 50 through the image memory 52 by step S4.

The thus fetched image data is processed by the data processing section 50 as will be explained later, so that judgement is made as to whether or not an immune reaction has occurred.

When the fetching of the image data for the first well has been finished, detection is made as to whether or not the CCD camera 20 is positioned at the last well in the first column in the microtiter plate 10 in the direction X. When the CCD camera 20 has not yet reached the final well, the operation is returned to step S3, so that the CCD camera 20 is moved by one pitch in the direction X up to the next well in the first column of the microtiter plate 10. As a result, the second well in the first column of the microtiter plate 10 is positioned right above the CCD camera 20.

In this state, the image data of the second well is fetched into the image memory 52 through the data processing section 50 and processed by the data processing section 50, so that judgement is made as to whether or not an immune reaction has occurred, in the same manner as in step S4. The same step as mentioned above is repeated.

When the fetching and processing of the image data for all the wells in the first column in the direction X are finished, the operation is moved onto step S5 at which YES is attained.

It is then judged whether or not the CCD camera 20 is at the last well in the direction Y by step S6.

When the CCD camera 20 has not yet reached the last well in the direction Y, the moving direction of the CCD camera 20 is reversed (X=−X) by step S7. Thus, the operation is returned to step S2. At that moment, the microtiter plate 10 is moved by one pitch in the direction X, and the fetching and processing of image data are repeated in the same manner as in steps S3 to S5.

When the successive fetching and processing of the image data for all the wells in the microtiter plate 10 are finished, the operation is moved onto step S6 at which YES is attained, so that the fetching of all the image data for one microtiter plate 10 is completed.

Figure 5:
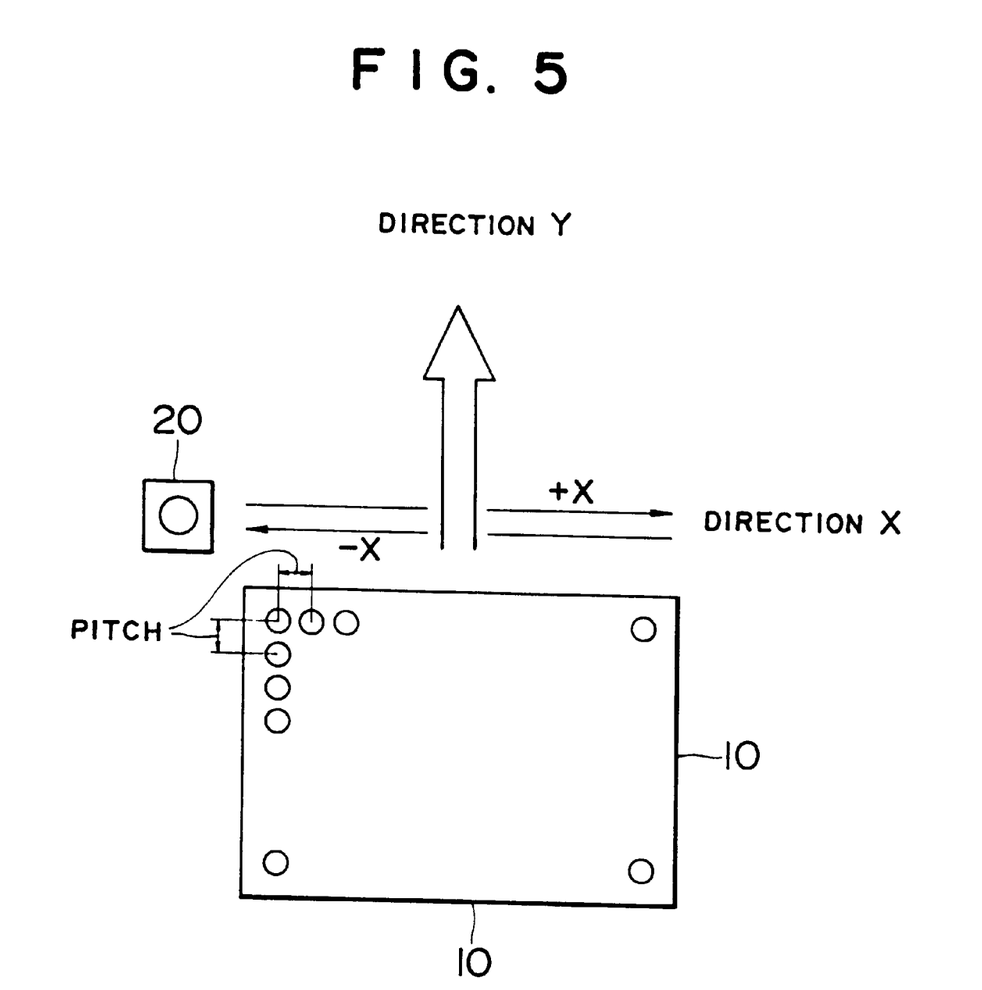
FIG. 5 is a diagram in explanation of an imaging operation for fetching image data from each well of a microtiter plate in the agglutination immunoassay system of the present invention.

More specifically, as illustrated in FIG. 5, when the CCD camera 20 is moved in the direction X and comes to the last well in the direction X, the microtiter plate 10 is moved by one pitch in the direction X. This operation is repeated, so that the image data for all the wells in the microtiter plate 10 are fetched.

When the magnetic-material containing particles are precipitated at the bottom of the well and allowed to stand at an inclination, the precipitated particles may flow along the bottom of the well under the influence of gravity to form a long and narrow spindle-shaped developed pattern.

A microtiter plate in general use includes a number of wells, for instance, 96 wells (8 wells in direction X and 12 wells in direction Y).

However, if the image data for all the wells is obtained by one imaging shot, the differences in the shot angle with respect to each well in one microtiter plate cannot be ignored, in particular, with respect to the wells in the peripheral portions of the microtiter plate.

The result is that the flowing direction of the precipitated magnetic-material containing particles in each well, when viewed from one imaging device, differs depending upon the location of the well in the microtiter plate. Accordingly, the length of the developed pattern of the flowed particles in each well is also differently observed depending upon the location of the well.

Thus, the shape of the developed pattern of the flowed, precipitated particles cannot be precisely detected or observed by a conventional apparatus using such a single imaging device.

In sharp contrast, in the present invention, image data or image signals are independently obtained from each well by an imaging device, so that the problems caused by the difference of the shot angle can be completely eliminated, and therefore the shape of the developed pattern of the flowed, precipitated particles can be accurately detected.

With reference to FIGS. 6 to 9, how the occurrence of an immune reaction is detected by processing the image data fetched into the data precessing section 50 from each well one by one will now be explained.

Figure 6:
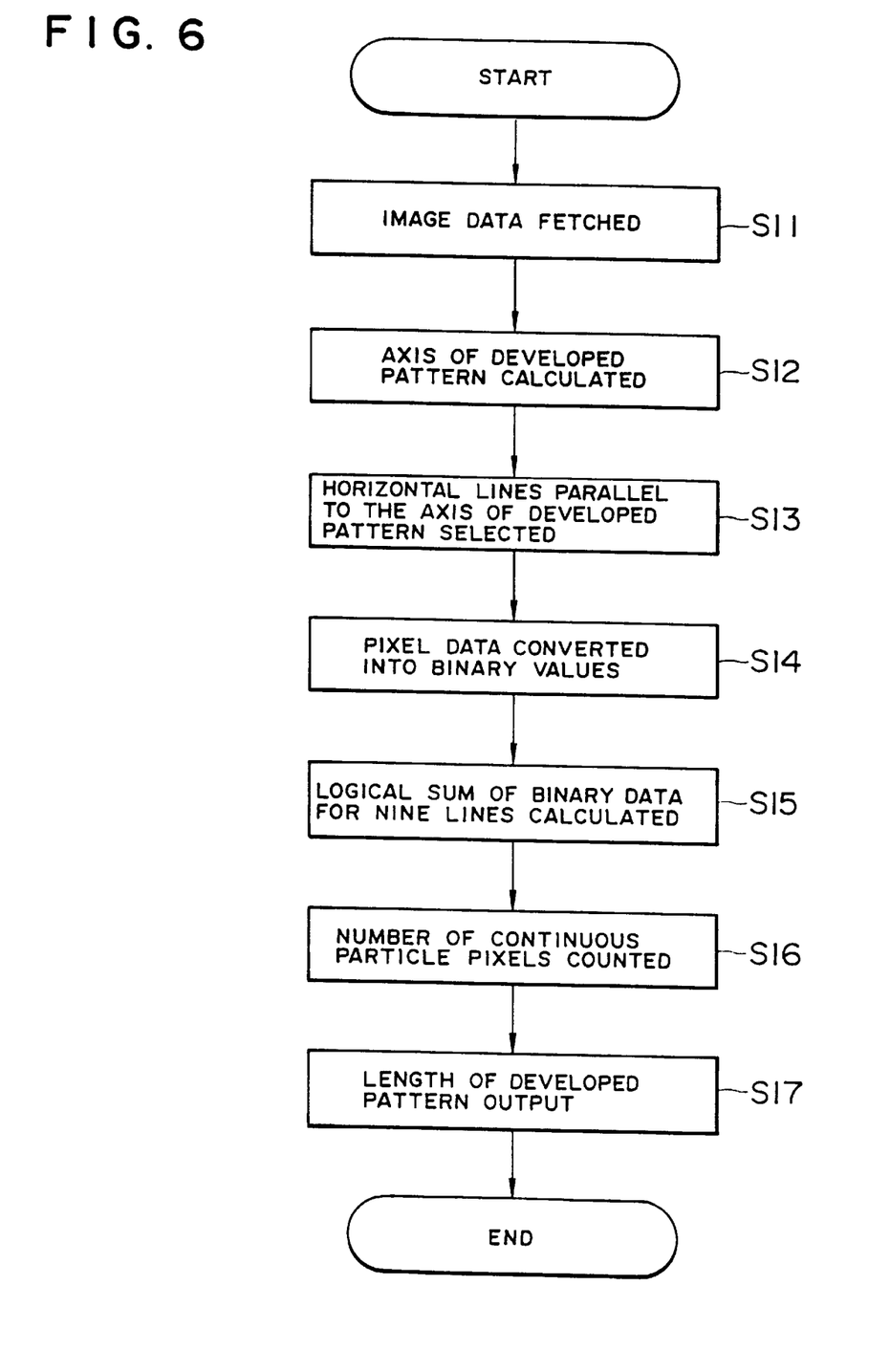
FIG. 6 is a flow chart in explanation of an image processing procedure in the agglutination immunoassay system of the present invention.

With reference to FIG. 6, the image data from one well is fetched by step S11.

In this example of the present invention, the quantity of image data that can be obtained by the CCD camera 20 from the developed pattern of the flowed, precipitated particles in each well is 512×128 pixels, with 256 gradations of lightness from 0 to 255. The smaller the value, the smaller the transparency or the greater the darkness. The value "0" is black.

Figure 7A:
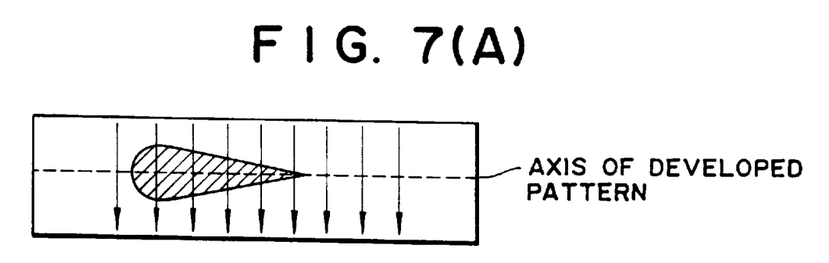
FIGS. 7(A) and FIG. 7(B) are respectively a diagram for determination of an axis of a developed pattern of flowed, precipitated particles obtained by the agglutination immunoassay system of the present invention.

As mentioned previously, when the magnetic-material containing particles are precipitated at the bottom of the well and allowed to stand at an inclination, a spindle-shaped developed pattern of the precipitated particles is formed, with an axis extending in the same direction as that of the inclination, for instance, as shown in FIG. 7(A).

This axis is referred to as the axis of the developed pattern of precipitated particles. The position of this axis is calculated and determined by step S12.

When the microtiter plate at an inclination is returned to a horizontal position for imaging the developed pattern of the flowed, precipitated particles by the CCD camera 20, the above-mentioned axis of the developed pattern of precipitated particles is also horizontal extending in the same as that the direction Y in which the precipitated particles have flowed, The developed pattern of the flowed, precipitated particles is imaged by the CCD camera 20, with the flowed, precipitated particles being positioned in such a horizontal position.

From the image signals obtained by the CCD camera 20, for instance, data of 32 lines with intervals of 16 pixels perpendicular to the horizontal direction Y, are picked up and a black portion in the developed pattern is determined.

The center of each of the perpendicular lines in the black portion is calculated, and the average of the values of the calculated centers is obtained, whereby the above-mentioned axis of the developed pattern of the precipitated particles is calculated and determined. The axis of the developed pattern may also be obtained by the method of least squares.

Figure 7B:
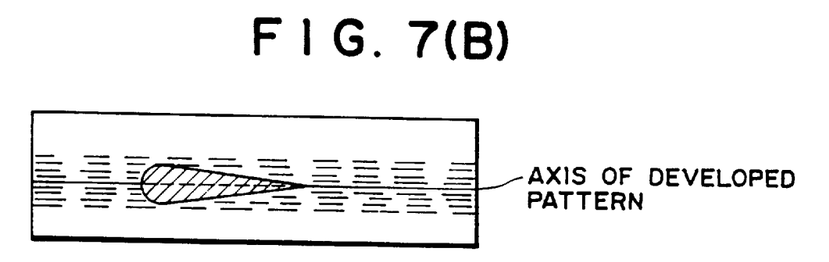

After the axis of the developed pattern of the precipitated particles is thus determined, for example, four horizontal lines which are above and parallel to the axis of the developed pattern of the precipitated particles, and another four horizontal lines which are below the axis and parallel to the axis are selected. Thus, a total of nine horizontal lines including the axis are selected as illustrated in FIG. 7(B) by step S13.

The pixel data of the above 9 horizontal lines are picked up.

Figure 8:
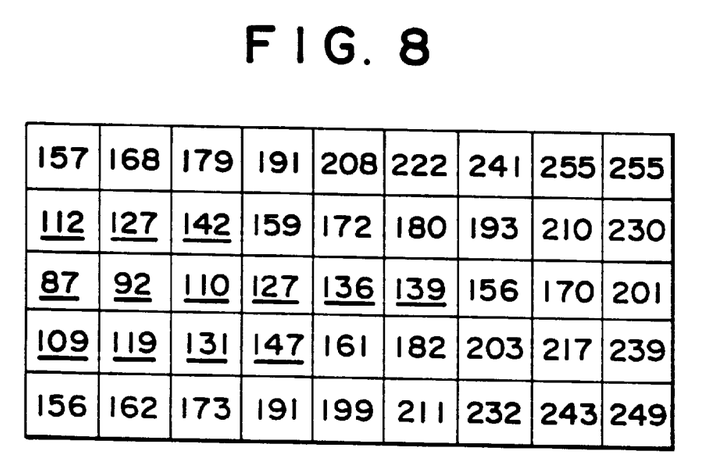
FIG. 8 is an example of image data obtained by the agglutination immunoassay system of the present invention.

FIG. 8 shows an example of such pixel data for 9 pixels×5 horizontal lines, just for explanation.

Figure 9:
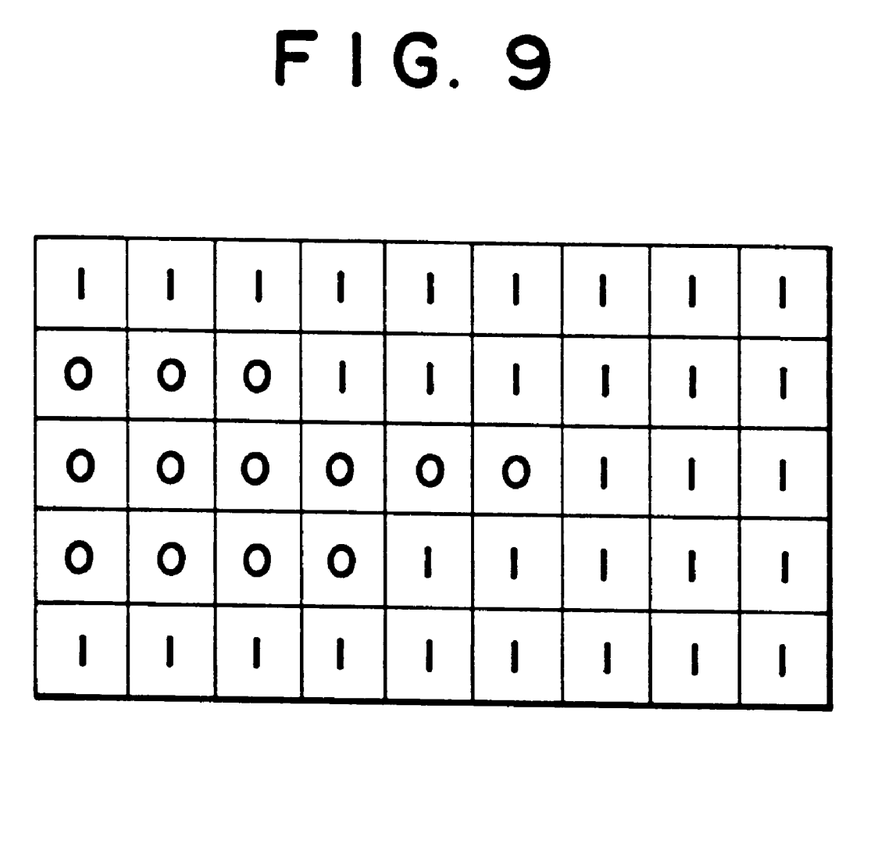
FIG. 9 is binary data converted from the data shown in FIG. 8.

The above picked up pixel data is then converted into binary values by use of a predetermined threshold value, such as [1], [0], by step S14. FIG. 9 shows the binary data converted from the data shown in FIG. 8 by using a threshold value of 150. In FIG. 9, the portions [0] are judged as "black" because of the presence of a particle pixel.

A logical sum of the binary data for the nine horizontal lines is calculated by step S15. In other words, even if there is only one [0] in the nine data in the vertical direction, the data at the corresponding horizontal position is made [0].

From the data for one line thus obtained, the number of pixels which continuously have a value of [0] is counted, whereby the length of the developed pattern of the flowed, precipitated particles pattern is calculated as a representative length of the developed pattern by step S16. The result of this calculation is output by step S17. Thus, a representative length of the developed pattern of the flowed, precipitated particles for each well can be determined.

When an immune reaction occurs, the precipitated particles agglutinate firmly with a relatively strong agglutination force, so that the precipitated particles hardly flow under the influence of gravity.

In contrast, when no immune reaction occurs, the precipitated particles do not agglutinate and therefore easily flow even under the influence of gravity.

Therefore, in accordance with the representative length of the representative length of the developed pattern of the flowed, precipitated particles, the presence or absence of an antibody or antigen in the test sample can be judged as (+) present, (−) absent or (±) equivocal.

For instance, the judgment is made by a length of 125 pixels or more as being "negative or absent (−)", a length of 75 pixels or less as being "positive or present (+)", and a length of 76 to 124 pixels as being (±) equivocal.

The results for all the wells in the microtiter plate 10 are thus printed out by the printer 36.

Figure 10:
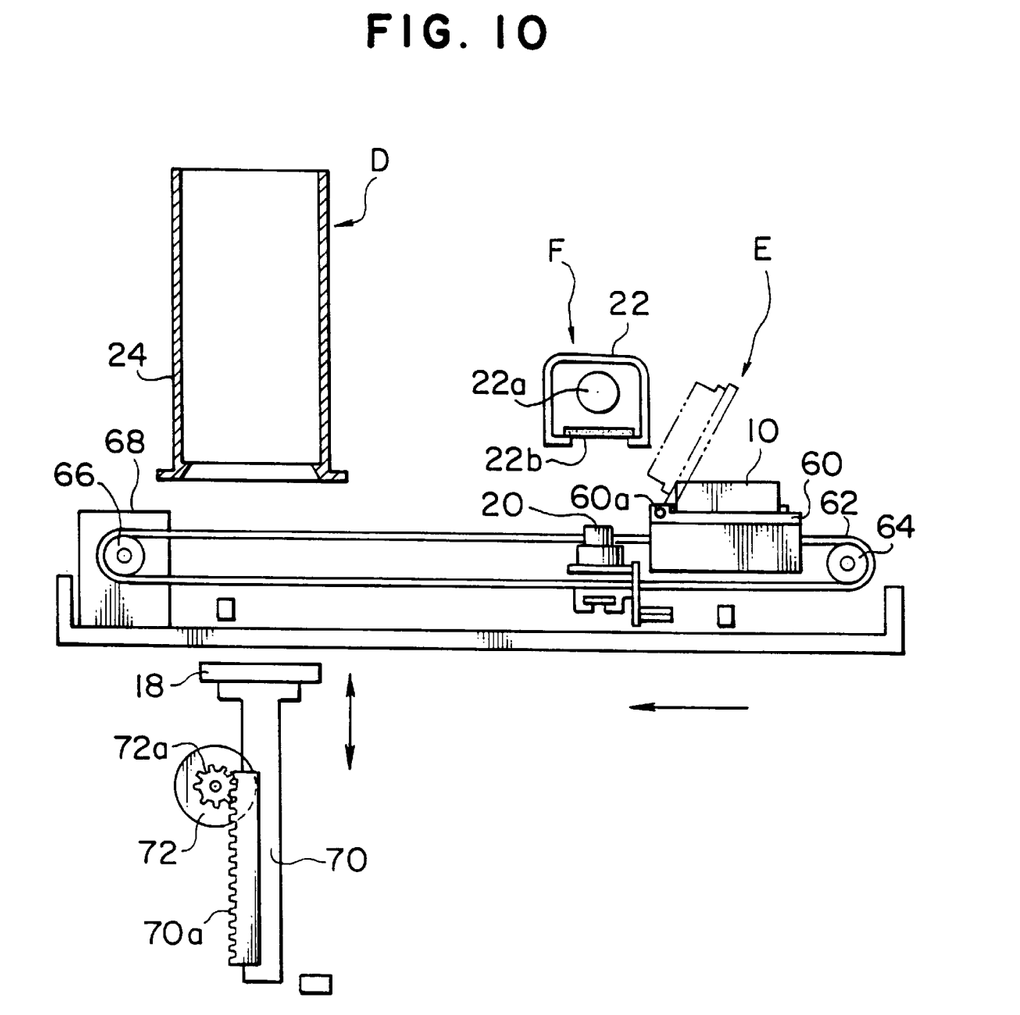
FIG. 10 is a schematic cross-sectional view of a transportation mechanism for a microtiter plate for use in the present invention.

FIG. 10 schematically shows a transportation mechanism for transporting the microtiter plate 10 from the inclination station E to the imaging station F to the magnetic precipitation and microtiter plate recovery station D.

The microtiter plate 10 is held by a holder 60. The holder 60 is in the shape of a frame and holds the peripheral portion of the microtiter plate 10. At one end portion of the holder 60 (on the left side thereof in FIG. 10), there is provided a rotating shaft 60a which extends in the direction X normal to the moving direction Y of the microtiter plate 10, so that the microtiter plate 10 can be inclined as indicated in FIG. 10 by the alternate long and short line in the inclination station E by the rotating shaft 60 with which a rotation drive mechanism (not shown) is engaged.

The holder 60 is attached to a belt 62 which is moved from the inclination station E to the magnetic precipitation and microtiter plate recovery station D. The belt 62 is disposed on the back side of this apparatus relative to the holder 60. The belt 62 is trained over a pair of pulleys 64 and 66. The pulley 66 can be driven in rotation by a stepping motor 68. By the rotation of the pulley 66 which is driven in rotation by the stepping motor 68, the microtiter plate 10 can be moved between each station and intermittently in the direction Y in the imaging station F.

The magnetic precipitation and microtiter plate recovery station D comprises a microtiter plate recovery stack 24 which is disposed above the belt 62, and the magnetic plate 18 which is disposed below the belt 62.

The magnetic plate 18 is mounted on the upper end of a rod 70 which is vertically movable by a motor 72.

The rod 70 is moved upward with the microtiter plate 10 being positioned on and held by the magnetic plate 18, whereby the magnetic-material containing particles in each well are precipitated by the application of magnetic force thereto.

After the imaging process, the rod 70 is moved upward with the microtiter plate 10 being placed on the magnetic plate 18, so that the microtiter plate 10 is inserted into the lower opening of the microtiter recovery stack 24, whereby the microtiter plate 10 is recovered and set in the microtiter recovery stack 24.

A pinion 72a is attached to the motor 72, and a rack 70a is attached to the rod 70, so that the rod 70 can be moved vertically by the rack 70a and pinion 72a.

In this apparatus, position detectors such as photoelectric sensors are provided in each unit.

Figure 11:
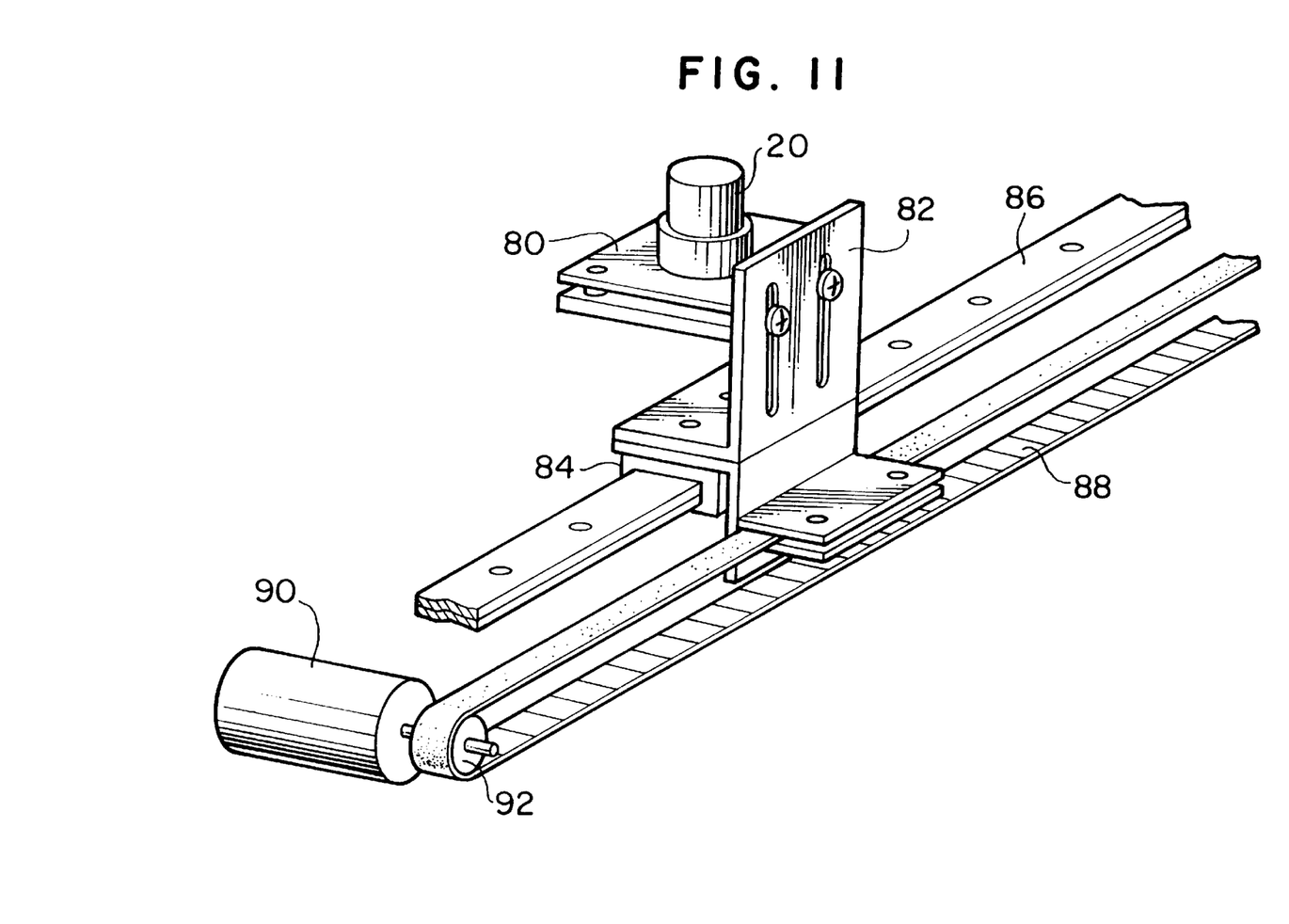
FIG. 11 is a schematic perspective view of a moving mechanism for a CCD camera for use in the present invention.

FIG. 11 is a perspective view of the moving mechanism for the CCD camera 20. As shown in FIG. 11, the CCD camera 20 is fixed to a support member 80. The support member 80 is also fixed to a guide member 84 through a support member 82. The guide member 84 holds a rail member 86 and is movable along the rail member 86.

The support member 82 is fixed to a belt 88. The belt 88 is trained over a pulley 92 which is rotated by a stepping motor 90. Thus, the CCD camera 20 can be moved by a predetermined distance by the rotational drive of the stepping motor 90.

Japanese Patent Applications Nos. 7-110960 and 7-110962 respectively filed May 9, 1995 are hereby incorporated by reference.

What is claimed is:

1. An apparatus for agglutination immunoassay comprising:

pipetting means for contacting, in a container, a test sample suspected of containing a desired analyte and a reagent comprising sensitized magnetic-material containing particles capable of reacting with and binding to said desired analyte;

magnetic precipitation means for precipitating said sensitized magnetic-material containing particles on the bottom of said container by the application of magnetic force;

inclination means for allowing said container to stand at an inclination so as to cause the precipitated sensitized magnetic-material containing particles to flow along the bottom of said container to form a developed pattern of said precipitated sensitized magnetic-material containing particles;

imaging means for imaging said developed pattern to obtain image data thereof and obtaining from said image data a representative length of said developed pattern of said precipitated sensitized magnetic-material containing particles in the flowing direction thereof; and immune reaction detection means for detecting the presence or absence of an immune reaction from said representative length of said developed pattern, thereby detecting the presence or absence of said desired analyte in said test sample.

2. The apparatus for agglutination immunoassay as claimed in claim 1, wherein said imaging means comprises a CCD camera.

* * * * *